United States Patent
Shuros et al.

(10) Patent No.: US 7,526,337 B2
(45) Date of Patent: Apr. 28, 2009

(54) METHOD AND DEVICE FOR LYMPHATIC SYSTEM MONITORING

(75) Inventors: Allan C. Shuros, St. Paul, MN (US); Michael J. Kane, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/422,417

(22) Filed: Jun. 6, 2006

(65) Prior Publication Data
US 2007/0282382 A1 Dec. 6, 2007

(51) Int. Cl.
*A61N 1/365* (2006.01)
(52) U.S. Cl. ........................................... 607/17
(58) Field of Classification Search ............. 607/6, 607/18, 22; 600/300, 301
See application file for complete search history.

(56) References Cited

U.S. PATENT DOCUMENTS

| | | | |
|---|---|---|---|
| 3,814,080 A | 6/1974 | Norman | |
| 3,916,875 A | 11/1975 | Toch | |
| 4,792,330 A | 12/1988 | Lazarus et al. | |
| 5,305,745 A * | 4/1994 | Zacouto | 600/324 |
| 5,391,143 A | 2/1995 | Kensey | |
| 5,655,548 A | 8/1997 | Nelson et al. | |
| 5,865,744 A | 2/1999 | Lemelson | |
| 6,024,704 A * | 2/2000 | Meador et al. | 600/486 |
| 6,106,477 A * | 8/2000 | Miesel et al. | 600/486 |
| 6,272,370 B1 | 8/2001 | Gillies et al. | |
| 6,368,274 B1 * | 4/2002 | Van Antwerp et al. | 600/365 |
| 6,370,417 B1 | 4/2002 | Horbaschek et al. | |
| 6,475,223 B1 | 11/2002 | Werp et al. | |
| 6,741,882 B2 | 5/2004 | Schaffter et al. | |
| 6,918,873 B1 * | 7/2005 | Millar et al. | 600/309 |
| 2001/0041870 A1 | 11/2001 | Gillis et al. | |
| 2002/0029037 A1 | 3/2002 | Kim | |
| 2002/0123674 A1 | 9/2002 | Plicchi et al. | |
| 2002/0188253 A1 | 12/2002 | Gordon et al. | |
| 2003/0105506 A1 | 6/2003 | Krishnan et al. | |
| 2003/0113303 A1 | 6/2003 | Schwartz | |
| 2003/0204185 A1 | 10/2003 | Sherman et al. | |
| 2004/0102804 A1 | 5/2004 | Chin | |

(Continued)

FOREIGN PATENT DOCUMENTS

WO WO-9314694 A1 8/2003

(Continued)

OTHER PUBLICATIONS

Knott, E. M., et al., "Increased lymphatic flow in the thoracic duct during manipulative intervention", *J Am Osteopath Assoc.*, 105(10), (Oct. 2005),447-56.

(Continued)

*Primary Examiner*—George R Evanisko
*Assistant Examiner*—Amanda Patton
(74) *Attorney, Agent, or Firm*—Schwegman, Lundberg & Woessner, P.A.

(57) ABSTRACT

A device and method are disclosed for physiological monitoring of the lymphatic system. An implantable device is configured with a lymphatic sensor disposed in a lymphatic vessel for sensing pressure, flow, and/or the concentration of particular markers within the vessel. The device may be further configured to deliver appropriate therapy in accordance with the lymphatic monitoring.

9 Claims, 3 Drawing Sheets

U.S. PATENT DOCUMENTS

| | | |
|---|---|---|
| 2004/0106953 A1 | 6/2004 | Yomtov et al. |
| 2004/0210118 A1 | 10/2004 | Letort |
| 2005/0043675 A1 | 2/2005 | Pastore et al. |
| 2005/0043894 A1* | 2/2005 | Fernandez .................... 702/19 |
| 2005/0049472 A1* | 3/2005 | Manda et al. ................ 600/345 |
| 2005/0075701 A1* | 4/2005 | Shafer .......................... 607/72 |
| 2005/0143765 A1 | 6/2005 | Bachmann et al. |
| 2005/0149014 A1 | 7/2005 | Hauck et al. |
| 2005/0267440 A1 | 12/2005 | Herman et al. |
| 2006/0020333 A1 | 1/2006 | Lashinski et al. |
| 2006/0074453 A1* | 4/2006 | Kieval et al. .................... 607/9 |
| 2007/0021731 A1 | 1/2007 | Garibaldi et al. |
| 2007/0282376 A1 | 12/2007 | Shuros |
| 2007/0282386 A1 | 12/2007 | Shuros |
| 2007/0282390 A1 | 12/2007 | Shuros |
| 2008/0009719 A1 | 1/2008 | Shuros et al. |

FOREIGN PATENT DOCUMENTS

| | | |
|---|---|---|
| WO | WO-03098177 A2 | 11/2003 |
| WO | WO-2004006795 A1 | 1/2004 |
| WO | WO-2005089863 A1 | 9/2005 |
| WO | WO-2007067690 A2 | 6/2007 |
| WO | WO-2007146489 A2 | 12/2007 |
| WO | WO-2007146493 A1 | 12/2007 |
| WO | WO-2007146517 A2 | 12/2007 |

OTHER PUBLICATIONS

Pulley, M. S., et al., "Intravenous, intralesional and endolymphatic administration of lymphokines in human cancer.", *Lymphokine Res., 5 Suppl 1*, (1986),S157-63.

"U.S. Appl. No. 11/422,423, Non-Final Office Action mailed Jan. 10, 2008", 12 pgs.

\* cited by examiner

METHOD AND DEVICE FOR LYMPHATIC SYSTEM MONITORING

RELATED APPLICATIONS

This application is related to co-pending application Ser. Nos. 11/422,423, 11/422,414, 11/422,418, and 11,422,421, all filed Jun. 6, 2006 and hereby incorporated by reference.

FIELD OF THE INVENTION

This invention pertains to methods and systems for diagnosing and treating disease with implantable devices.

BACKGROUND

The lymphatic system and the cardiovascular system are closely related structures that are joined by a capillary system. The lymphatic system is important to the body's defense mechanisms by filtering out organisms that cause disease and producing lymphocytes that attack foreign organisms and generate antibodies. It is also important for the distribution of fluids and nutrients in the body, because it drains excess fluids and protein from interstitial tissues. Lymph is the fluid that seeps outside the blood vessels in interstitial spaces of body tissues and is then absorbed by lymphatic capillaries to flow back into the bloodstream through the lymphatic vessels. The terminal structures of the lymphatic vessels include the right lymphatic duct, which drains lymph fluid from the upper right quarter of the body above the diaphragm and down the midline, and the thoracic duct, located in the mediastinum of the pleural cavity which drains the rest of the body. Through the flow of blood in and out of arteries, into the veins, and through the lymph vessels and nodes, the body is able to eliminate the products of cellular breakdown and bacterial invasion.

SUMMARY

A device and method are disclosed for physiological monitoring of the lymphatic system. An implantable device is configured with a lymphatic sensor disposed in a lymphatic vessel for sensing pressure, flow, and/or the concentration of particular markers within the vessel. The device may be further configured to deliver appropriate therapy in accordance with the lymphatic monitoring.

DETAILED DESCRIPTION

Figure 1:
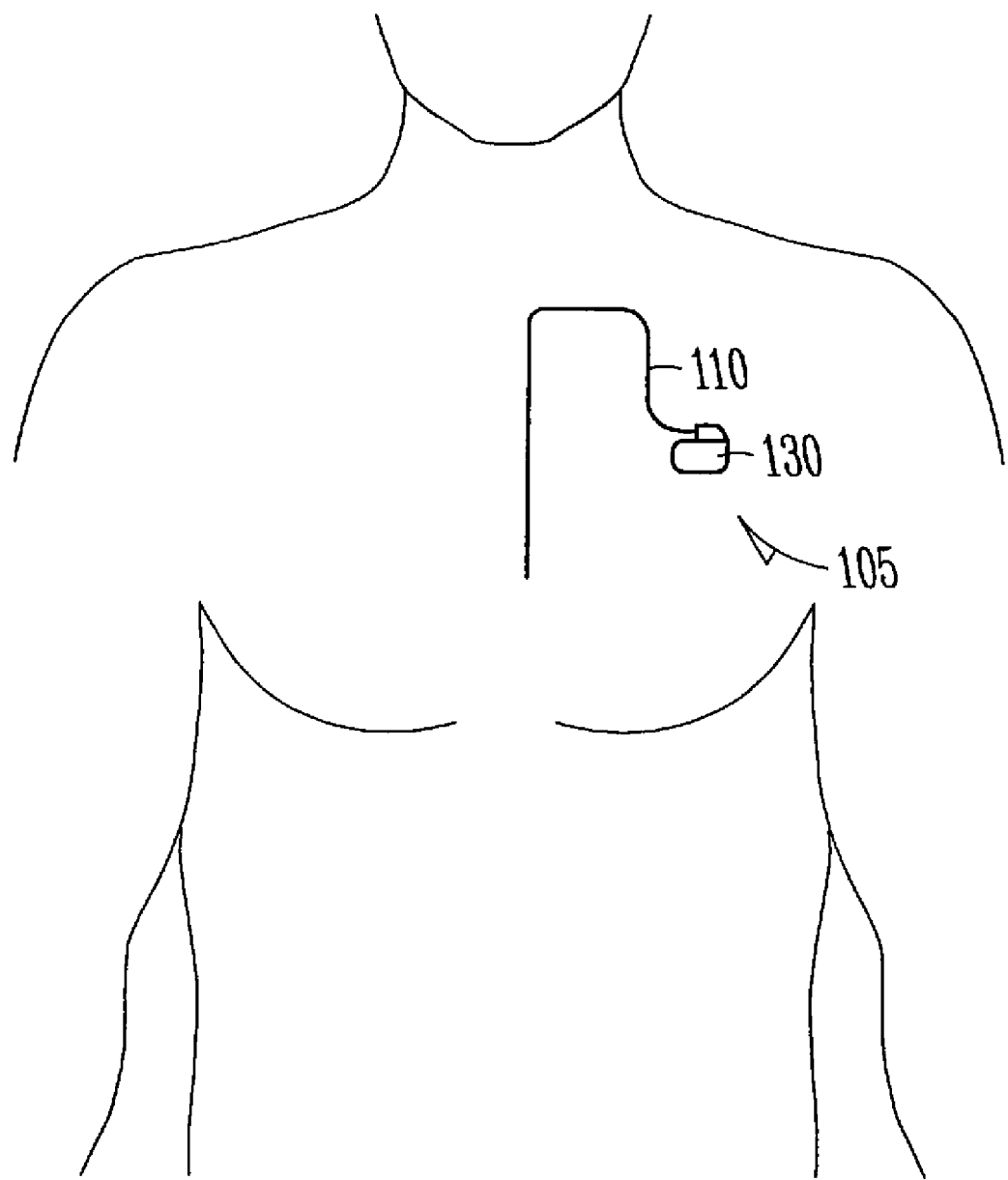
FIG. 1 illustrates the physical placement of an implanted monitoring device and attached lead.

This disclosure relates to a device and method for monitoring lymphatic function. The lymphatic vessels are part of the body's circulatory system and serve as a pathway by which fluids can flow from the interstitial spaces into blood. Lymphatic vessels also communicate with lymph nodes and facilitate the body's immune function by transporting foreign antigens to the lymph nodes from the interstitial spaces. As described below, an implantable device may be used to monitor lymphatic function and thereby detect particular conditions such as increased inflammation and edema.

One of the functions performed by the lymphatic system is the conveying back to the blood of fluid and proteins exuded from the blood vessels into the interstitial space. Exuded fluid and proteins are absorbed by lymphatic capillaries and then flow into the venous system through lymphatic vessels. The lymphatic system is normally very efficient at removing excess fluid from the interstitial space and is even able to maintain a slight negative pressure. Under certain conditions, however, the lymphatic system is so overwhelmed with fluid that a buildup occurs, referred to as edema. When edema occurs, pressure and flow within the lymphatic vessels increases. As described below, an implantable device may be configured to measure these parameters and detect edema. The concentration of particular molecules in the lymphatic fluid may also be detected by the device in order to further characterize edema or detect other clinical states of interest. The device may also be configured to deliver a specific therapy in response to the monitoring of lymphatic function, such as when edema is detected.

In one embodiment, a lymphatic function monitor may be incorporated as part of a cardiac pacing device configured to deliver cardiac resynchronization therapy (CRT) in which pacing pulses are used to overcome conduction deficits and cause the heart to contract in a more coordinated manner (e.g., biventricular pacing). CRT is commonly used to treat patients with chronic heart failure. When chronic heart failure worsens, the decreased cardiac output causes diminished renal perfusion. The kidneys compensate for this by absorbing more salt and water from the renal filtrate which raises venous pressure. The increased venous pressure then results in edema when the fluid buildup into the interstitial space overcomes the lymphatic system's ability to remove it. Edema due to heart failure may occur, for example, in the lung or in the extremities. In one embodiment, an implantable device configured to monitor lymphatic function may be further configured to initiate, increase, or modulate the delivery of CRT when edema is detected. The device could also be programmed to adjust certain CRT parameters such as the atrioventricular delay interval when edema is detected.

Edema can also be caused by kidney disease or liver disease that results in decreased plasma proteins, particularly albumin. This causes increases osmotic pressure that forces more fluid from the blood capillaries into the interstitium. In another embodiment, the device is configured to deliver an appropriate medication when edema is detected (e.g., an ACE inhibitor or angiotensin receptor blocker for the treatment of kidney disease.)

The composition of lymphatic fluid may also be monitored to determine if particular clinical states exist. For example, the concentration of cytokines and immunoglobulins may be used to assess certain autoimmune diseases and cancer. When the concentration of such substances reaches a particular level, the device may then be configured to deliver an appropriate medication.

FIG. 1 shows an exemplary physical placement of an implantable monitoring device as described herein. In one embodiment, an implantable monitoring device 105 is placed subcutaneously on the patient's chest or abdomen, similar to a standard cardiac pacemaker. The monitoring device is connected to one or more leads 110, each having a distal member that incorporates an electrode or sensor for sensing physiological parameter(s) related to lymphatic function, referred to herein as a lymphatic sensor. The lead is positioned within the lymphatic system using a venous approach which involves initial entry into the venous blood system. In the embodiment depicted in FIG. 1, the lead 110 passes subcutaneously from the device housing 130 to a point of venous access in the upper chest or neck such as the subclavian vein. The lead is then guided into the thoracic duct ostium using standard fluoroscopy techniques and positioned at a selected location within the lymphatic system. An alternative implantation approach includes placing the lymphatic sensor using a direct surgical approach.

Figure 2:
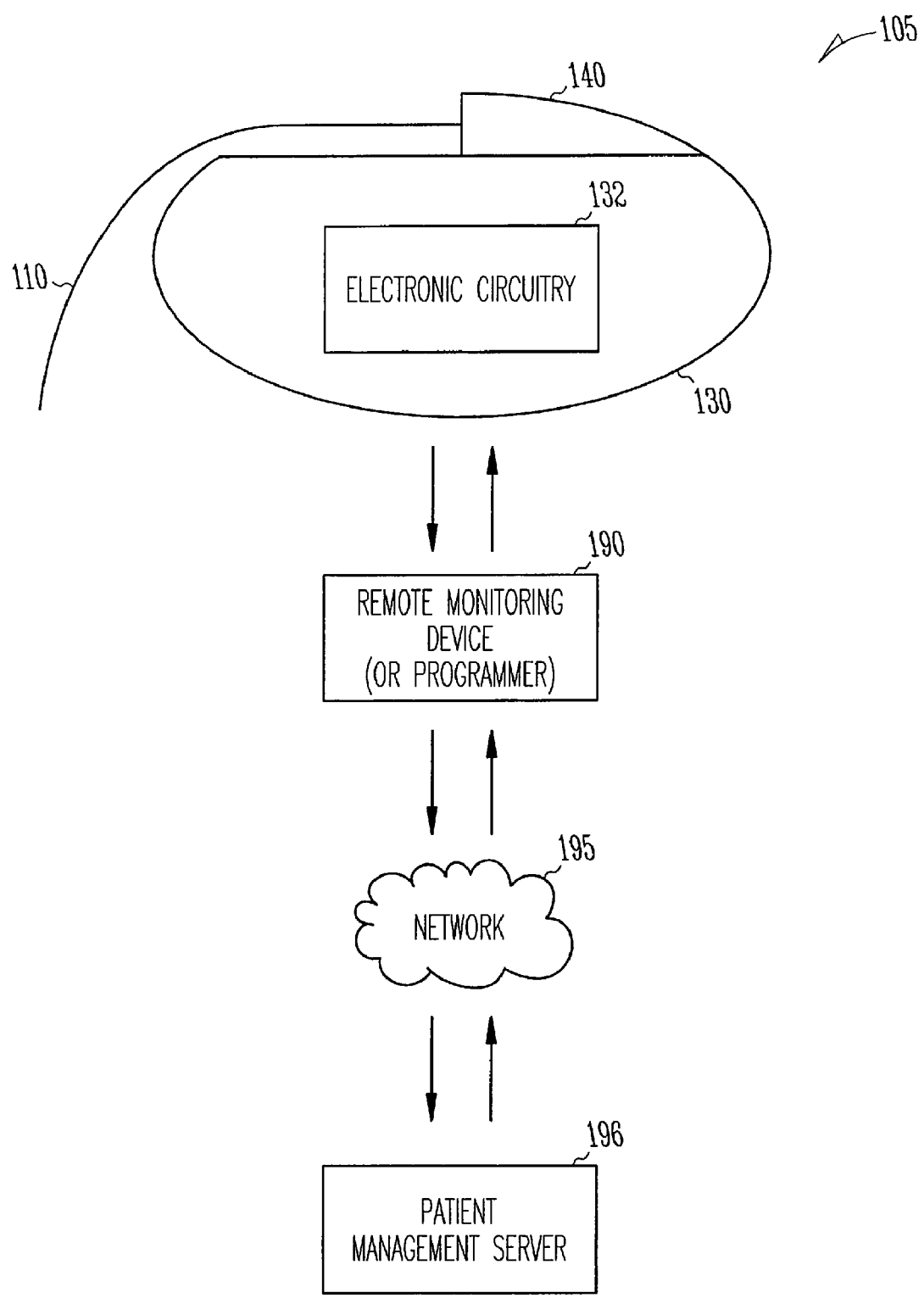
FIG. 2 illustrates the components of an exemplary system for physiological monitoring of the lymphatic system.

FIG. 2 shows an exemplary monitoring system. The pulse monitoring device 105 includes a hermetically sealed housing 130 that is placed subcutaneously or submuscularly in a patient's chest or other convenient location as noted above. The housing 130 may be formed from a conductive metal, such as titanium, and may serve as an electrode for delivering electrical stimulation with a unipolar lead. A header 140, which may be formed of an insulating material, is mounted on the housing 130 for receiving the leads 110 which are electrically connected to the circuitry within the housing. Contained within the housing 130 is the electronic circuitry 132 for providing the functionality to the device as described herein which may include a power supply, monitoring circuitry, therapy circuitry, and a programmable electronic controller for controlling the operation of the device.

Figure 3:
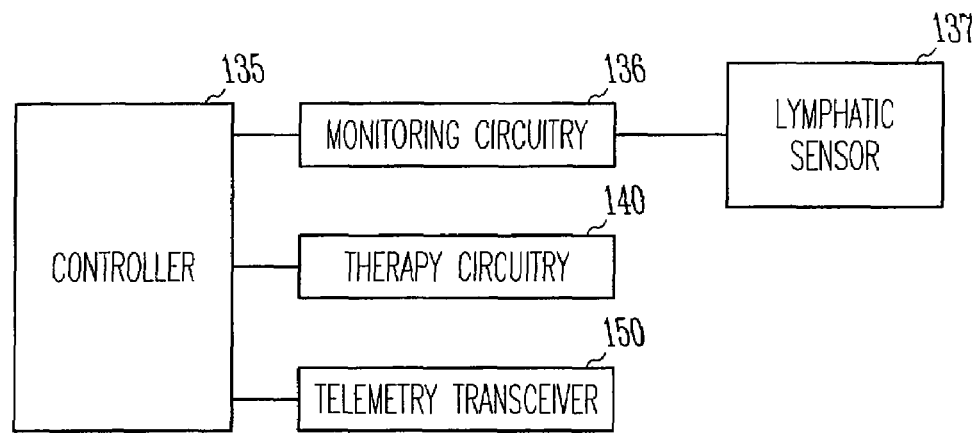
FIG. 3 illustrates a block diagram of the components of an exemplary implantable monitoring device.

FIG. 3 illustrates exemplary components of the electronic circuitry 132 depicted in FIG. 2. A controller 135 is provided which may be made up of discrete circuit elements but is preferably a processing element such as a microprocessor together with associated memory for program and data storage which may be programmed to perform algorithms for delivering therapy. (As the terms are used herein, "circuitry" and "controller" may refer either to a programmed processor or to dedicated hardware components configured to perform a particular task.) The controller is interfaced to monitoring circuitry 136 from which it receives data generated by one or more lymphatic sensors 137. The monitoring circuitry may include, for example, circuitry for amplification, filtering, and/or analog-to-digital conversion of voltages generated by a lymphatic sensor.

In one embodiment, the lymphatic sensor 137 is a flow or pressure sensor for sensing conditions within a lymphatic vessel that indicate edema may be present. As noted above, edema may be diagnosed when the lymphatic vessels are overwhelmed with fluid due to, for example, elevated venous pressure caused by heart failure and renal compensation thereof, kidney disease, or liver disease. Under such conditions, the pressure and/or flow of lymph within the lymphatic vessels may be increased. In another embodiment, the lymphatic sensor is a chemo-sensor designed to generate a voltage proportional to the concentration of a particular chemical species. The chemo-sensor may be used to provide the controller an indication of the concentration of a particular molecule in the lymphatic fluid that is of interest, referred to as a marker. Examples of markers whose concentrations may be of diagnostic value include immunoglobulins, cytokines, or specific proteins that could be used to characterize a particular disease state. Such chemo-sensors may use immobilized antibodies with binding affinities specific for the different marker antigens. Upon formation of an Ab-Ag complex between the antibody and the marker, the chemo-sensor may produce an electrical signal by, for example, incorporating a piezoelectric transducer that responds to mechanical stresses induced by the Ab-Ag complex or a transducer that responds to potential changes resulting from the Ab-Ag complex.

In another embodiment, the lymphatic sensor is a stretch or volume sensor that monitors the degree of stretch or change in volume within a lymphatic vessel using impedance, ultrasonics, acoustic, capacitance, inductance, or optical-type instruments. In another embodiment, the lymphatic sensor is a pulsatile rate sensor using impedance, ultrasonics, acoustic, piezoelectric, piezoresistive, capacitance, inductance, or optical type instruments to monitor pulsatile flow within a lymphatic vessel or a pulsatile contractility sensor that measures intensity of peristaltic wave motion using impedance, ultrasonics, acoustic, capacitance, inductance, or optical type instruments. In another embodiment, the lymphatic sensor is a density sensor for detecting the concentration of dissolved and suspended particulates in the lymph fluid using an optical, acoustic, or electrical instrument. In another embodiment, the lymphatic sensor is a cell counting sensor that detects the density of lymphocytes in the lymph fluid.

Figure 4:
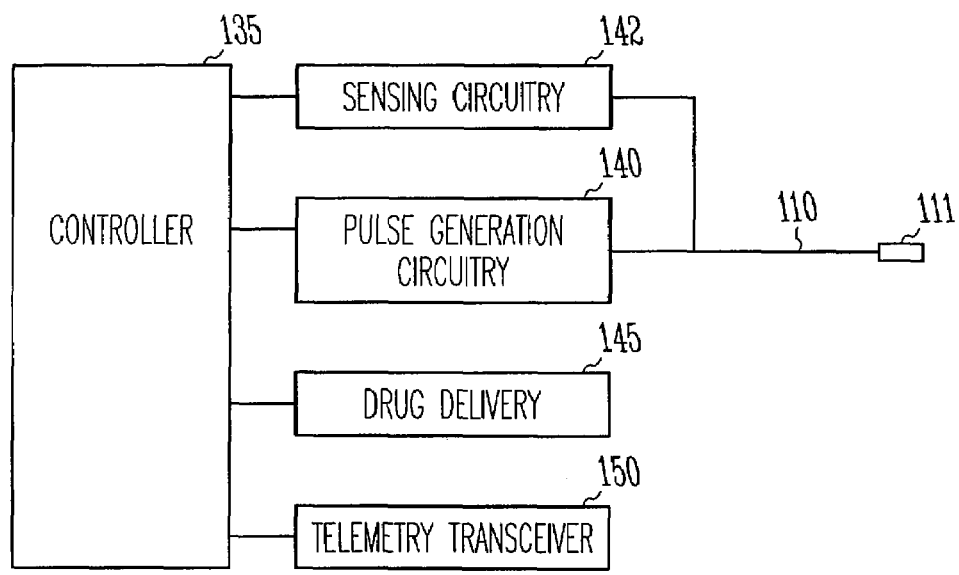
FIG. 4 illustrates an embodiment for delivering cardiac pacing therapy.

In the embodiment illustrated in FIG. 3, the controller 135 is also interfaced to therapy circuitry 140 in order to control the delivery of therapy by the device in response to conditions sensed by the monitoring circuitry. The therapy circuitry 135 may include circuitry for delivery of one or more therapy modalities such as cardiac resynchronization therapy, neural stimulation, and drug therapy. In one embodiment, shown in FIG. 4, the device includes circuitry for delivering bradycardia cardiac pacing and/or cardiac resynchronization therapy and includes pulse generation circuitry 140, cardiac sensing circuitry 142, and pacing/sensing electrodes 111 electrically connected to the device by leads (i.e., intravenous leads such as shown in FIG. 1) adapted for disposition in the heart. In another embodiment, the device includes a drug delivery device 145 actuated by the therapy circuitry that may be used to deliver medication in response detection of particular conditions. Such medications could include anti-inflammatory drugs, cancer chemotherapeutic agents, diuretics, or cardiac drugs.

Also interfaced to the controller in FIG. 3 is a telemetry transceiver 150 capable of communicating with an external programmer or a remote monitoring device 190 as illustrated in FIG. 2. An external programmer wirelessly communicates with the device 105 and enables a clinician to receive data and modify the programming of the controller. A remote monitoring device similarly communicates with the device 105 and is further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

In order to implant a lead incorporating a lymphatic sensor(s) into a selected location within lymphatic vessel, the lymphatic system may be visualized using lymphangiography. In this technique, dye is injected into the subcutaneous tissue of an extremity such as the foot, or other peripheral lymph vessel, and the lymphatic system drains the dye making the lymphatic vessels visible. A lymphatic vessel is cannulated, and radiopaque contrast is injected to illuminate major lymph vessels including the thoracic duct and its ostium into the subclavian vein. A catheter or the lead may then be guided into the thoracic duct ostium via the venous system using fluoroscopy techniques and positioned at a selected location within the lymphatic system. Initial cannulation of the lymph ostium with a guide wire or catheter may be achieved through the left or right subclavian vein, the left jugular veins, the epigastric/mammary veins or the femoral veins. In order to facilitate navigation through the lymphatic vessels and position the sensor at a selected anatomical location, an overlapping technique may be employed whereby fluoroscopic images produced by the injected dye are used in conjunction with anatomical images of the patient produced by other modalities such as conventional x-ray, CAT scans, MRI scans, or ultrasonic scans. The fluoroscopic image may be overlaid with the anatomical image and the lead then guided to the selected location.

To implant the lead, a catheter or the lead by itself may be introduced into the venous system and from there into the thoracic duct ostium using conventional over-the-wire techniques that employ a guide wire. The guide wire is manually or mechanically pushed and manipulated to guide its travel and upon which catheters and/or leads may be advanced. A stereotaxis technique in which external magnets or other means are used to guide the catheter may also be used to improve maneuverability and precision as well as provide increased safety. An example of this technique is described in U.S. Pat. No. 6,475,223, hereby incorporated by reference. Once the catheter or lead is in the lymphatic system, it must also traverse valves in the lymphatic vessels whose function is to allow flow of lymphatic fluid in only one direction to the thoracic duct. In the case where a catheter is employed, as the catheter is guided through a vessel to one of these valves, the catheter may incorporate a vacuum system to open the valves. When the vacuum system is actuated, it draws negative pressure to create a pressure gradient that opens the valve. An alternative technique for opening lymphatic valves involves using a catheter incorporating a compliant balloon on its distal tip. When the catheter reaches a lymphatic valve, the balloon is inflated to mechanically dilate the vessel which opens the valve and allows a wire or the catheter to pass through. In still another technique, the catheter incorporates an electrode at its tip that is used to cause smooth muscle contraction of the lymphatic vessel. Such smooth muscle contraction can create a pressure gradient that opens the valve and allows the catheter to advance past the valve.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method, comprising:
    implanting a cardiac pacing device that includes lymphatic monitoring circuitry;
    implanting a lead electrically connected to the lymphatic monitoring circuitry into a lymphatic vessel, the lead having a lymphatic sensor incorporated therein for sensing a physiological parameter related to lymphatic function;
    processing sensing signals generated by the lymphatic sensor via the monitoring circuitry to detect the presence of edema; and,
    modifying delivery of cardiac pacing therapy when edema is detected from the lymphatic sensor signals.

2. The method of claim 1 wherein the lymphatic sensor is a pressure sensor.

3. The method of claim 1 wherein the lymphatic sensor is a flow sensor.

4. The method of claim 1 wherein the lymphatic sensor is a chemo-sensor for generating a voltage proportional to the concentration of a particular chemical species.

5. The method of claim 1 further comprising transmitting an alarm message via a telemetry transceiver if a value sensed by the lymphatic sensor reaches a specified limit value.

6. The method of claim 1 further comprising delivering therapy based upon sensing signals generated by the lymphatic sensor.

7. The method of claim 6 further comprising delivering cardiac resynchronization therapy based upon sensing signals generated by the lymphatic sensor.

8. The method of claim 7 further comprising initiating or increasing the delivery of cardiac resynchronization therapy upon sensing a lymphatic flow or pressure value indicative of edema.

9. The method of claim 7 further comprising adjusting one or more cardiac resynchronization parameters upon sensing a lymphatic flow or pressure value indicative of edema.

* * * * *